United States Patent
Bacik et al.

(10) Patent No.: US 8,153,078 B2
(45) Date of Patent: *Apr. 10, 2012

(54) TRANSPORTABLE DECONTAMINATION UNIT AND DECONTAMINATION PROCESS

(75) Inventors: Michael A. Bacik, Fairview, PA (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 12/033,901

(22) Filed: Feb. 20, 2008

(65) Prior Publication Data
US 2008/0267819 A1  Oct. 30, 2008

Related U.S. Application Data

(60) Provisional application No. 60/893,134, filed on Mar. 6, 2007, provisional application No. 60/962,876, filed on Aug. 1, 2007.

(51) Int. Cl.
*A61L 2/00* (2006.01)
*A61L 9/00* (2006.01)
*B01J 19/00* (2006.01)
(52) U.S. Cl. .................... 422/292; 422/291; 422/29
(58) Field of Classification Search ............. 422/29, 422/291, 292
See application file for complete search history.

(56) References Cited

U.S. PATENT DOCUMENTS

| | | | |
|---|---|---|---|
| 2,285,849 A | 2/1940 | Wallace | 290/1 |
| 2,348,574 A | 5/1944 | Ross | 21/96 |
| 2,630,537 A | 3/1953 | Wiegman et al. | 290/1 |
| 2,823,863 A | 2/1958 | Moyes | 237/2 |
| 3,858,645 A | 1/1975 | Egger | 165/66 |
| 3,994,684 A | 11/1976 | Tomasulo | 21/91 |
| 4,675,923 A | 6/1987 | Ashley | 4/599 |
| 4,808,377 A | 2/1989 | Childers et al. | 422/26 |
| 4,858,256 A | 8/1989 | Shankman | 4/597 |
| 4,861,560 A | 8/1989 | Nakajima | 422/111 |
| 4,909,988 A | 3/1990 | Childers et al. | 422/26 |
| 4,993,199 A | 2/1991 | Hughes | 51/426 |
| 5,114,670 A | 5/1992 | Duffey | 422/24 |
| 5,258,162 A | 11/1993 | Andersson et al. | 422/28 |
| 5,277,875 A | 1/1994 | Albright et al. | 422/109 |
| 5,286,447 A | 2/1994 | Fannin et al. | 422/28 |
| 5,405,587 A | 4/1995 | Fernandez et al. | 422/292 |
| 5,472,004 A | 12/1995 | Gilliard | 134/111 |

(Continued)

FOREIGN PATENT DOCUMENTS

EP    1 393 751 A1    3/2004
(Continued)

OTHER PUBLICATIONS

Hardigg Cases, Modular Storage Shipping Boxes, 2005, (www.militarycases.com/MobilMaster.html).

(Continued)

*Primary Examiner* — Kevin Joyner
(74) *Attorney, Agent, or Firm* — Renner, Otto, Boisselle & Sklar, LLP

(57) ABSTRACT

The disclosed invention relates to a portable decontamination unit. The invention also relates to a decontamination process. The decontamination unit may employ a shipping container for transporting a decontaminant generator and optionally a power generator, and for functioning as a decontamination chamber. The decontamination unit may be ruggedized for use in hostile environments such as those that may be anticipated for military applications.

9 Claims, 6 Drawing Sheets

U.S. PATENT DOCUMENTS

| | | | | |
|---|---|---|---|---|
| 5,502,975 | A | 4/1996 | Brickley et al. | 62/94 |
| 5,520,893 | A | 5/1996 | Kasting, Jr. et al. | 422/305 |
| 5,634,880 | A | 6/1997 | Feldman et al. | 600/132 |
| 5,665,316 | A | 9/1997 | Salonia et al. | 422/113 |
| 5,706,846 | A | 1/1998 | Sutton | 135/128 |
| 5,868,667 | A | 2/1999 | Lin et al. | 600/133 |
| 5,882,590 | A | 3/1999 | Stewart et al. | 422/28 |
| 5,916,096 | A | 6/1999 | Wiesmann et al. | 52/63 |
| 5,958,336 | A | 9/1999 | Duarte | 422/24 |
| 6,077,480 | A | 6/2000 | Edwards et al. | 422/28 |
| 6,120,739 | A | 9/2000 | Thomas et al. | 422/186.07 |
| 6,199,388 | B1 | 3/2001 | Fischer, Jr. | 62/90 |
| 6,279,589 | B1 * | 8/2001 | Goodley | 134/102.1 |
| 6,313,543 | B1 | 11/2001 | Frank | 290/1 A |
| 6,488,902 | B1 | 12/2002 | DeCato et al. | 423/210 |
| 6,517,639 | B2 | 2/2003 | Toepfer et al. | 134/21 |
| 6,557,365 | B2 | 5/2003 | Dinnage et al. | 62/271 |
| 6,645,450 | B2 | 11/2003 | Stoltz et al. | 423/245.2 |
| 6,711,907 | B2 | 3/2004 | Dinnage et al. | 62/94 |
| 6,734,405 | B2 | 5/2004 | Centanni et al. | 219/628 |
| 6,751,964 | B2 | 6/2004 | Fischer | 62/94 |
| 6,852,279 | B2 | 2/2005 | Williams et al. | 422/4 |
| 6,867,393 | B1 | 3/2005 | Lewis | 219/401 |
| 6,906,296 | B2 | 6/2005 | Centanni et al. | 219/628 |
| 6,923,716 | B2 | 8/2005 | Koeger | 454/230 |
| 6,928,143 | B2 | 8/2005 | Menear et al. | 378/69 |
| 6,936,434 | B2 | 8/2005 | McDonnell et al. | 435/31 |
| 6,953,549 | B2 | 10/2005 | Hill et al. | 422/30 |
| 6,986,386 | B2 | 1/2006 | Sekhar et al. | 165/214 |
| 7,047,751 | B2 | 5/2006 | Dinnage et al. | 62/94 |
| 7,102,052 | B2 | 9/2006 | McVey et al. | 588/303 |
| 7,144,550 | B2 | 12/2006 | Devine et al. | 422/28 |
| 7,146,962 | B2 | 12/2006 | Sugimoto et al. | 123/198 |
| 7,160,566 | B2 | 1/2007 | Fink et al. | 426/235 |
| 7,203,979 | B2 | 4/2007 | O'Brien | 4/900 |
| 7,308,798 | B2 | 12/2007 | Caggiano | 62/63 |
| 2002/0015672 | A1 | 2/2002 | Saint-Martin et al. | 422/295 |
| 2003/0129111 | A1 | 7/2003 | Miller et al. | 422/292 |
| 2003/0133834 | A1 | 7/2003 | Karle | 422/33 |
| 2003/0138347 | A1 | 7/2003 | Lin | 422/28 |
| 2003/0164091 | A1 | 9/2003 | Hill et al. | 95/90 |
| 2004/0057868 | A1 * | 3/2004 | McVey et al. | 422/28 |
| 2004/0184950 | A1 | 9/2004 | McVey et al. | 422/4 |
| 2004/0197252 | A1 | 10/2004 | Parrish | 423/235 |
| 2005/0005533 | A1 | 1/2005 | Stewart et al. | 52/79.1 |
| 2005/0220666 | A1 | 10/2005 | Foster | 422/28 |
| 2006/0008379 | A1 | 1/2006 | Mielnik et al. | 422/32 |
| 2006/0018788 | A1 | 1/2006 | Monico et al. | 422/26 |
| 2006/0099121 | A1 | 5/2006 | Doona et al. | 422/292 |
| 2006/0252974 | A1 | 11/2006 | McVey et al. | 588/299 |
| 2006/0270887 | A1 | 11/2006 | Watkins | 588/300 |
| 2006/0289490 | A1 | 12/2006 | Mielnik | 219/628 |
| 2007/0098592 | A1 | 5/2007 | Buczynski et al. | 422/3 |
| 2007/0274858 | A1 | 11/2007 | Childers et al. | 422/28 |

FOREIGN PATENT DOCUMENTS

| | | |
|---|---|---|
| FR | 2 515 408 | 10/1981 |
| WO | 00/57929 | 10/2000 |
| WO | 02/066082 A1 | 8/2002 |
| WO | 2004/110504 A1 | 12/2004 |

OTHER PUBLICATIONS

International Search Report and Written Opinion, Application No. PCT/US2008/054340, mailed Jun. 30, 2008.

* cited by examiner

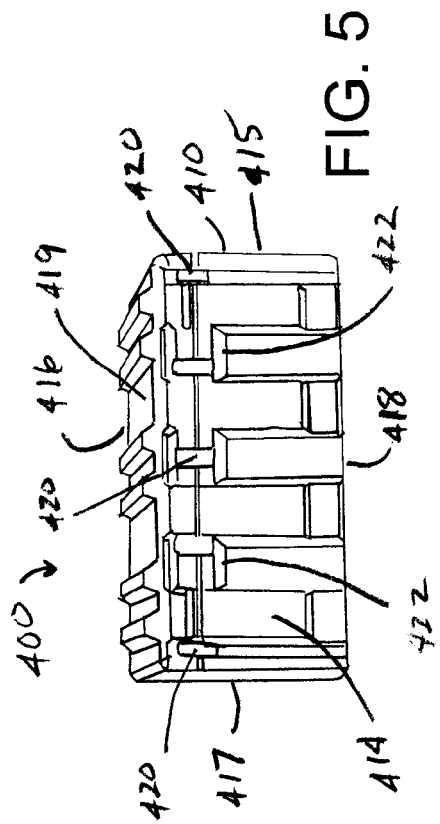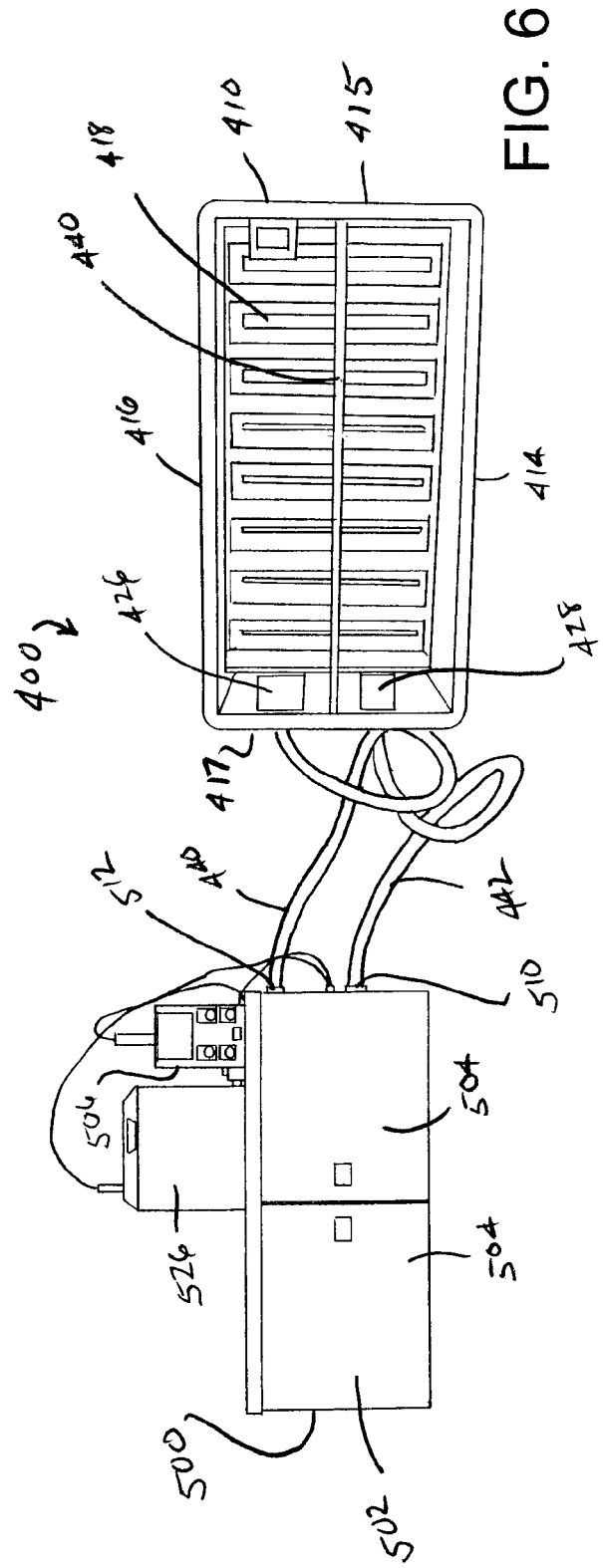

TRANSPORTABLE DECONTAMINATION UNIT AND DECONTAMINATION PROCESS

This application claims benefit under 35 U.S.C. §119(e) to U.S. Provisional Application Ser. No. 60/893,134, filed Mar. 6, 2007, and U.S. Provisional Application Ser. No. 60/962,876, filed Aug. 1, 2007. These applications are incorporated herein by reference in their entireties.

TECHNICAL FIELD

This invention relates to a transportable decontamination unit and to a decontamination process.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

It would be advantageous for the military to use these decontaminant systems in the field in defense against chemical and biological weapons. However, there might be problems with this due to the fact that when operating in the field, suitable enclosures for containing the decontaminant while conducting the decontamination process are typically not readily available. The decontaminant system could be transported to the point of use in the field along with a suitable decontamination chamber. However, a problem with this relates to the fact that the military strives to reduce the logistical burden associated with its field operations in order to reduce the cost and complexity of its supply chain. Thus, the transport of a decontamination chamber along with the decontamination system to the point of use in the field would be regarded as not being feasible. This invention provides a solution to this problem.

This invention relates to a transportable decontamination unit, comprising: a shipping container and a decontaminant generator, the shipping container being suitable for transporting the decontaminant generator, the shipping container being suitable for use as a decontamination chamber, the shipping container including at least one gas inlet for admitting a decontaminant air stream into the shipping container and at least one gas outlet for removing gas from the shipping container; and the decontaminant generator being adapted for generating a decontaminant air stream, the decontaminant generator being adapted for being stored in the shipping container during transport of the shipping container and being removed from the shipping container when used to conduct a decontamination, the decontaminant generator having a decontaminant air stream outlet which is adapted to be connected to the gas inlet of the shipping container, the decontaminant generator having a gas inlet which is adapted to be connected to the gas outlet of the shipping container.

In one embodiment, the decontamination unit further comprises a power generator, the power generator being adapted for generating power to operate the decontaminant generator, the power generator being adapted for being stored in the shipping container during transport of the shipping container and being removed from the shipping container when used to conduct a decontamination.

This invention relates to a process for operating the foregoing decontamination unit, the process comprising; opening the shipping container; removing the decontaminant generator from the shipping container, connecting the gas inlet of the shipping container to the gas outlet of the decontaminant generator with a first hose; connecting the gas outlet of the shipping container to the gas inlet of the decontaminant generator with a second hose; placing one or more contaminated articles in the shipping container; closing the shipping container; generating a decontaminant air stream in the decontaminant generator, the decontaminant air stream comprising a decontaminant and air; flowing the decontaminant air stream into the shipping container; contacting the contaminated articles in the shipping container with the decontaminant air stream to decontaminate the contaminated articles; flowing gas from the shipping container to the decontaminant generator; opening the shipping container; and removing decontaminated articles from the shipping container.

BRIEF DESCRIPTION OF THE DRAWINGS

In the annexed drawings all parts and features have like references. A number of the annexed drawings are schematic illustrations which are not necessarily proportioned accurately or drawn to scale.

FIG. 5 is a schematic illustration of an alternate embodiment of the shipping container which may be used with the inventive decontamination unit. This shipping container may function as a shipping container during transport of the decontamination unit, and as a decontamination chamber during operation of the decontamination unit.

FIG. 6 is a schematic illustration of the inventive decontamination unit using the shipping container illustrated in FIG. 5, the shipping container having been converted to a decontamination chamber. A decontaminant generator used with the decontamination unit is removed from the interior of the shipping container and attached to the exterior of the shipping container by removable hoses.

DETAILED DESCRIPTION

Figure 1:
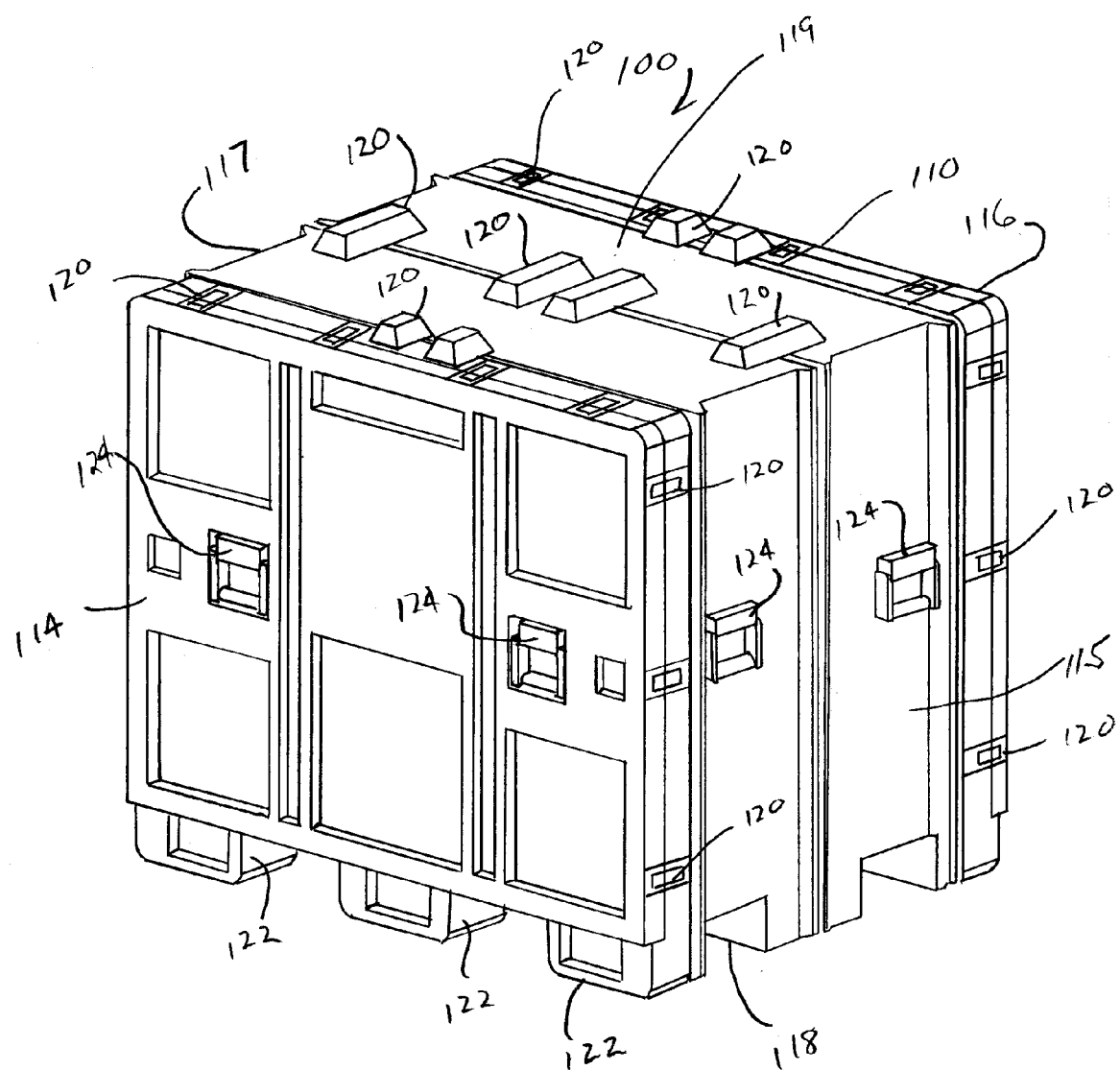
FIG. 1 is a schematic illustration of a shipping container which is suitable for use with the inventive decontamination unit. The shipping container may function as a shipping container during transport of the decontamination unit, and as a decontamination chamber during operation of the decontamination unit.
Figure 2:
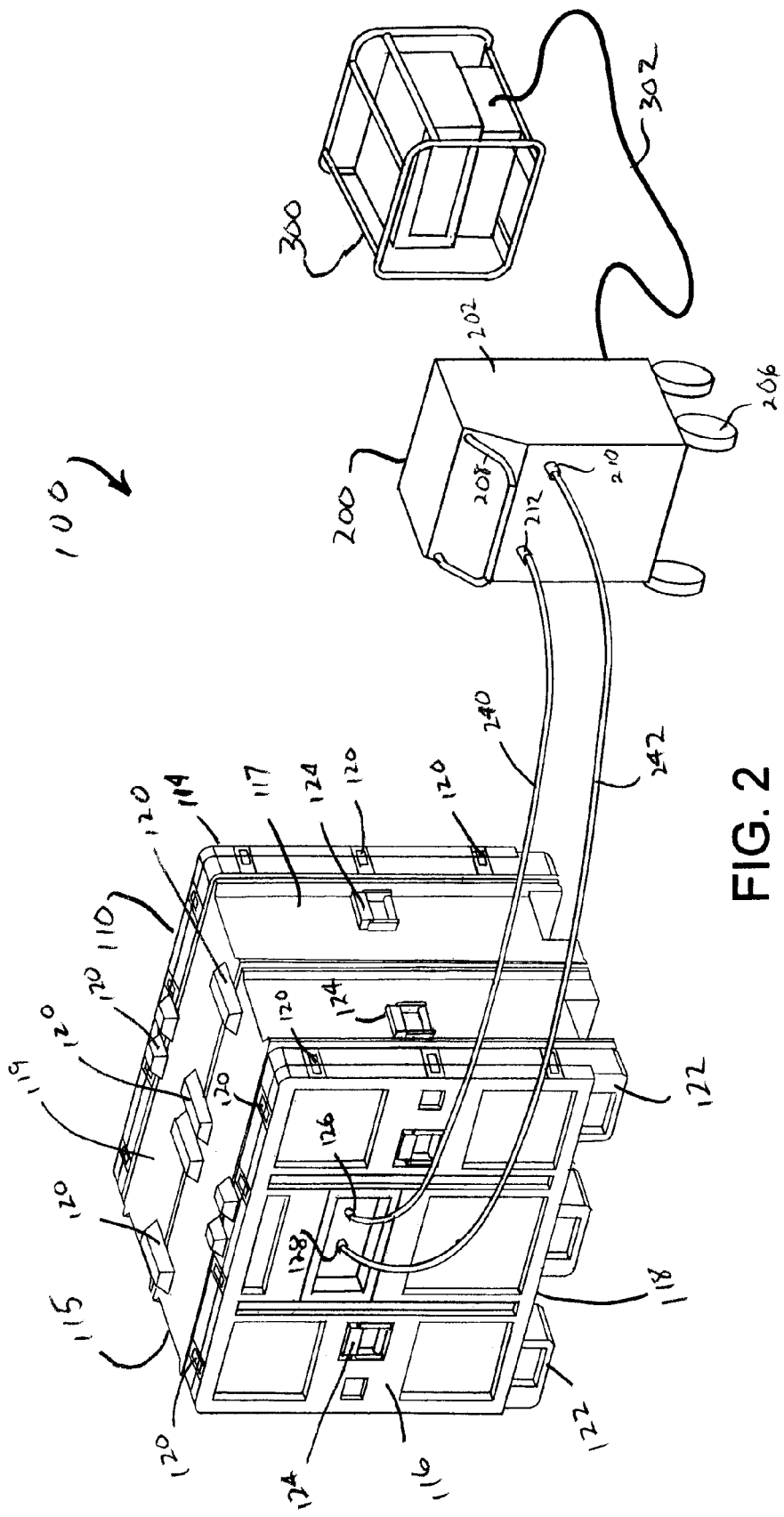
FIG. 2 is a schematic illustration of the inventive decontamination unit with the shipping container illustrated in FIG. 1 converted to a decontamination chamber. A decontaminant generator used with the decontamination unit is removed from the interior of the shipping container and attached to the exterior of the shipping container by removable hoses. A power generator, which optionally may be transported in the shipping container, is attached to the decontaminant generator by an electrical cord.
Figure 3:
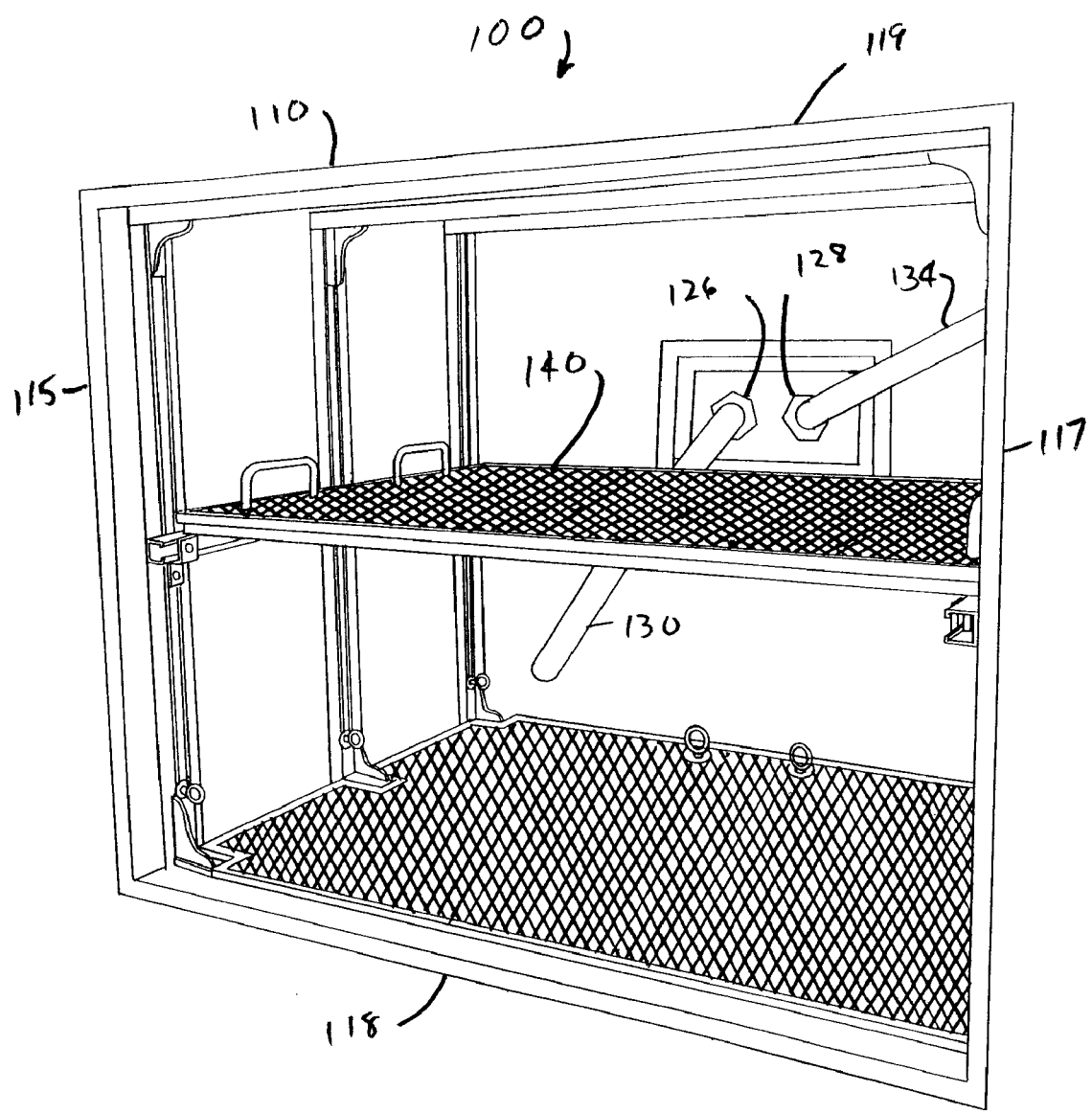
FIG. 3 is a schematic illustration of the interior of the shipping container illustrated in FIG. 1.
Figure 4:
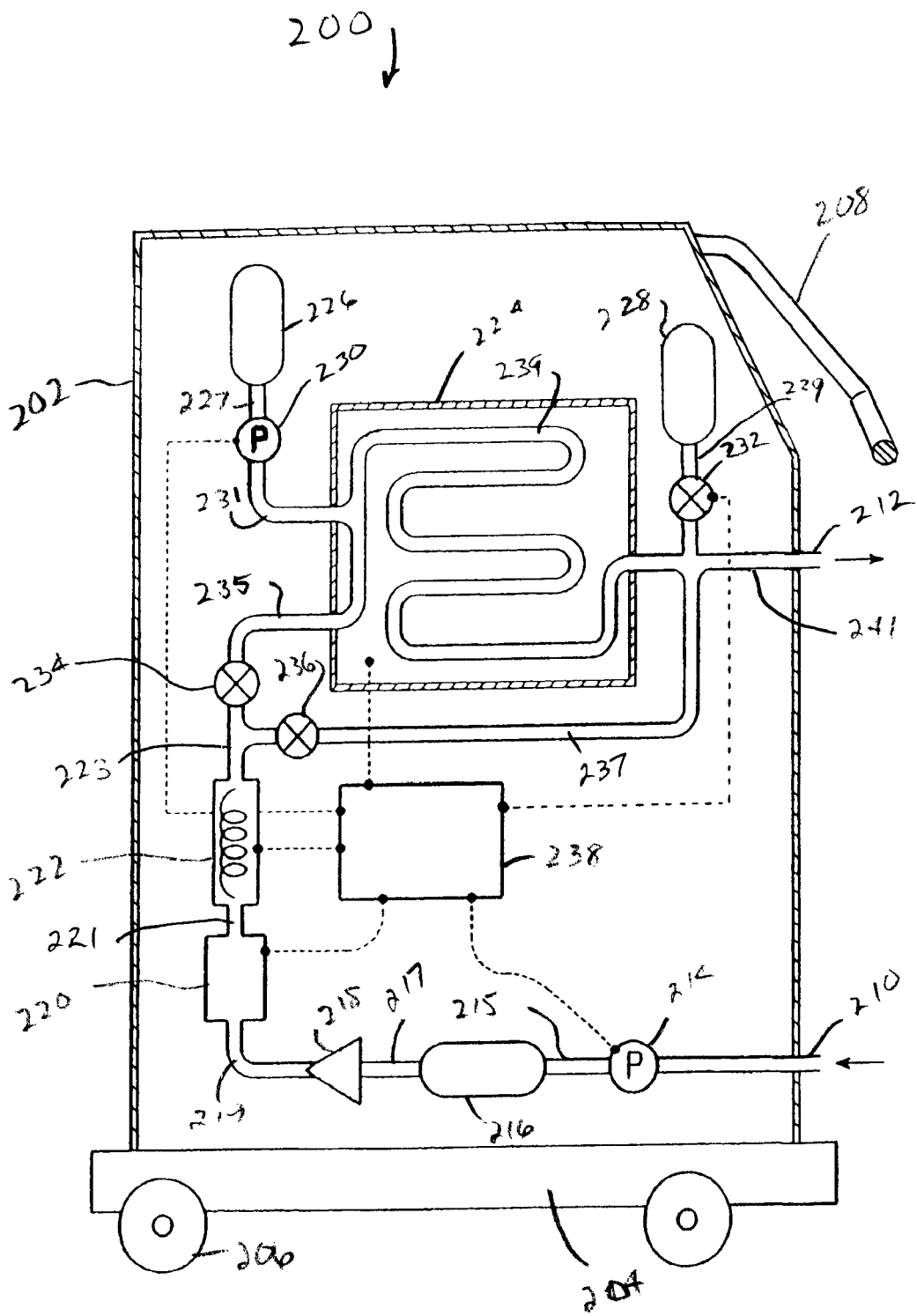
FIG. 4 is a flow sheet showing the operation of the decontaminant generator illustrated in FIG. 2.

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

The term "line" when referring to the drawings may refer to any conduit for conveying a fluid. The conduit may be in any desired form, for example, one or more hoses, pipes, tubings, channels, and the like. These may be made of materials sufficient to provide the required properties of strength, flexibility, and resistance to the fluids being conveyed. The lines may be ruggedized to permit use in hostile environments such as those that may be encountered in military applications.

The inventive decontamination unit, in its illustrated embodiments, will be described initially with reference to FIGS. 1-4. Referring to FIGS. 1-4, decontamination unit 100 comprises shipping container 110. Shipping container 110 is suitable for storing and transporting decontaminant generator chamber 200, and optionally power generator 300. The shipping container 110 may be converted to a decontamination chamber in order to conduct a decontamination process using the inventive decontamination unit 100. Shipping container 110 includes sides 114, 115, 116 and 117, bottom 118, and top 119. Shipping container 110 includes latch mechanisms 120 for opening and closing the shipping container 110. Shipping container 110 includes lifting brackets 122 to facilitate lifting the shipping container with, for example, a fork lift, and the like. Shipping container 110 includes handles 124 to facilitate lifting the shipping container.

The shipping container 110 may be of sufficient size to provide for the storage and transport of the decontaminant generator 200, and optionally, the power generator 300, and to provide a decontamination chamber of sufficient scale to accommodate the needs for the desired decontamination process. The shipping container may also be of sufficient size to provide for the storage and transport of hoses, power cables, and other ancillary equipment necessary to provide for a "complete" decontamination system ready for use in the field. The shipping container 110 may be sufficiently lightweight to be readily transportable. The shipping container may be sufficiently air tight to permit operation of the decontamination process in the shipping container at a slightly negative internal pressure, that is, a pressure within the shipping container up to about 10 inches of water below atmospheric pressure, and in one embodiment in the range from about 0.01 to about 5 inches of water below atmospheric pressure, and in one embodiment in the range from about 0.01 to about 2 inches, and in one embodiment in the range from about 0.01 to about 1 inch, and in one embodiment in the range from about 0.01 to about 0.3 inch of water below atmospheric pressure. The shipping container 110 may have an internal volume in the range from about 0.5 to about 2 cubic meters, and in one embodiment in the range from about 0.5 to about 1.5 cubic meters, and in one embodiment in the range from about 0.7 to about 1.2 cubic meters, and in one embodiment from about 0.9 to about 1.1 cubic meters, and in one embodiment about 1 cubic meter. The shipping container 110 may have a height (as measured from the bottom 118 to the top 119) in the range from about 0.5 to about 2.5 meters, and in one embodiment in the range from about 0.7 to about 2 meters, and in one embodiment in the range from about 1 to about 1.5 meters. The shipping container 110 may have a width (as measured from side 114 to side 116) in the range from about 0.6 to about 1.5 meters, and in one embodiment in the range from about 0.8 to about 1.2 meters, and in one embodiment in the range from about 1 to about 1.2 meters. The shipping container 110 may have a length (as measured from side 115 to side 117) in the range from about 0.7 to about 2 meters, and in one embodiment in the range from about 1 to about 1.5 meters, and in one embodiment in the range from about 1.2 to about 1.4 meters. The overall weight of the shipping container 110, when loaded with decontaminant generator 200, and optionally the power generator 300, may be in the range from about 200 to about 700 pounds (90.7 to 317.5 Kg), and in one embodiment in the range from about 300 to about 600 pounds (136.1 to 272.2 Kg). The shipping container 110 may be readily transported using conventional techniques, for example, the shipping container 110 may be transported by airplane, ship, truck, and the like. The shipping container 110 may be transported using a military standard 463L master pallet.

The shipping container 110 may comprise a shipping case available from Hardigg under the tradename MobilMaster 8. The MobilMaster 8, which is illustrated in FIG. 1, has outer dimensions of 1.31×1.06×1.18 meters, an internal volume of 1.01 cubic meters, and a shipping weight of 124.74 Kg. The MobilMaster 8 is made of rotational molded polyethylene, and is designed to stack two high for a total of eight per 463L pallet.

The 463L master pallet may be the main device used for air transport by the United States Air Force. Cargo aircraft used by the United States Air Force may be configured to accept these pallets. The 463L pallets may also be used for combat offloads and aerial delivery or airdrop. The 463L pallet is 88 inches (224 cm) wide, 108 inches (274 cm) long, and 2.25 inches (5.7 cm) high. The usable space is 84 inches (213 cm) by 104 inches (264 cm). The 463L pallet may hold up to 10,000 pounds (4500 Kg) of cargo. The empty weight is 290 pounds (130 Kg). The 463L pallet is built of a balsa wood core and surrounded by a thin aluminum skin. There are 22 rings surrounding the edge, each rated at 7,500 pounds (3400 Kg).

In the practice of the inventive decontamination process, the shipping container 110 may be opened, and the decontaminant generator 200, and optionally the power generator 300, may be removed from the shipping container 110. The shipping container 110 is equipped with gas inlet 126 and gas outlet 128. The gas inlet 126 and gas outlet 128 may be connected to hoses 240 and 242. The hoses 240 and 242 may extend from the gas inlet 126 and gas outlet 128 to the decontaminant generator 200 to provide for the flow of a decontaminant air stream from the decontaminant generator 200 to the gas inlet 126, and the flow of gas from the gas outlet 128 back to the decontaminant generator 200. Internal conduit 130 may extend from the gas inlet 126 to interior of the shipping container 110. Internal conduit 134 may extend from the gas outlet 128 to the interior of the shipping container 110. The shipping container 110 may be equipped with bulkhead connections to facilitate the use of concentration monitors, etc. The decontaminant generator 200 may be connected to power generator 300 by cord 302. The articles to be decontaminated may be placed in the shipping container 110 and the shipping container 110 may then be closed. A decontaminant air stream may flow from the decontaminant generator 200 through hose 240 to gas inlet 126, from gas inlet 126 through conduit 130 into the interior of the shipping container 110. When used in the operation of the inventive decontamination process, the shipping container 110 may be referred to as a decontamination chamber. The decontaminant air stream may circulate in the interior of the shipping container/decontamination chamber 110, contact contaminated articles positioned in the shipping container/decontamination chamber 110, and decontaminate the contaminated articles. A gaseous air stream comprising spent gases (i.e., air, residual decontaminant, residual hazardous biological and/or chemical materials, etc.) may flow through conduit 134 to gas outlet 128, and from gas outlet 128 through hose 242 back to the decontaminant generator 200.

The shipping container 110 may include interior shelves 140. The shelves 140 may be used to facilitate placement of the decontaminant generator 200 and, optionally, the power generator 300, and related ancillary equipment, in the shipping container 110 during storage and transport of the shipping container 110, and/or to facilitate placement of contaminated articles in the shipping container/decontamination chamber during operation of the decontamination process. Any desired number of shelves 140 may be used. The shelves 140 may be removable. The shelves 140 may be perforated or grated. The use of perforated or grated shelves may be advantageous to permit enhanced gas circulation within the shipping container/decontamination chamber 110.

The decontaminant generator 200 may comprise housing 202. The housing 202 may include base 204. The housing 202 may be supported by wheels 206. Handle 208 may be mounted on the side of the housing 202 and used to facilitate movement of the decontaminant generator 200. The decontaminant generator 200 may include gas inlet 210, gas outlet 212, blower 214, catalytic converter 216, filter 218, desiccant cartridge 220, heater 222, vaporizer 224, liquid decontaminant container 226, alkaline gas container 228, pump 230, regulator valve 232, and valves 234 and 236.

The decontaminant generator 200 may occupy a space in the shipping container 110 equal to about 30% to about 95% of the internal volume of the shipping container 110, and in one embodiment from about 40% to about 70% of the internal volume, and in one embodiment about 50% of the internal volume of the shipping container 110. The decontaminant generator 200 may occupy a space having the dimensions of about 62.9×102.8×94.9 cm. The decontaminant generator 200 may have a weight in the range from about 100 to about 500 pounds (45.4 to 226.8 Kg), and in one embodiment in the range from about 100 to about 200 pounds (45.4 to 90.7 Kg), and in one embodiment about 150 pounds (68 Kg).

In the operation of the decontaminant generator 200, a gaseous air stream comprising spent gases from the decontamination process may flow from the shipping container/decontamination chamber 110 through hose 242 back to the decontaminant generator 200. The gaseous air stream may enter the decontaminant generator 200 through gas inlet 210. The gaseous air stream may be forced by blower 214 through line 215 to and through catalytic converter 216. The catalytic converter 216 may be used to destroy residual amounts of the decontaminant that may be in the gaseous air stream. For example, the catalytic converter 216 may be use to convert residual hydrogen peroxide to water vapor and oxygen. The catalyst may comprise any transition metal, transition metal oxide, or combination thereof, having the desired catalytic properties. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The gaseous air stream may then flow through line 217 to and through filter 218. The filter 218 may comprise a carbon filter and a high efficiency particle air (HEPA) filter. The gaseous air stream may then flow through line 219 to desiccant cartridge 220 where water may be separated out. The desiccant cartridge 220 may contain a desiccant material such as lithium chloride, silica gel, molecular sieves, and the like. The desiccant material may be used to absorb moisture from the gaseous air stream and thereby dehumidify the gaseous air stream. The gaseous air stream may flow from the desiccant cartridge 220 through line 221 to heater 222 where it may be heated. The gaseous air stream may flow from the heater 222 through line 223, valve 234 and line 235 into line 239 in vaporizer 224. Liquid decontaminant may flow from liquid decontaminant container 226 through line 227 to pump 230, and from pump 230 through line 231 into line 239 in the vaporizer 224. The liquid decontaminant may be combined with the gaseous air stream in line 239. The liquid decontaminant may be vaporized in line 239 with the result being the formation of a vaporous decontaminant air mixture. The vaporous decontaminant air mixture may flow out of the vaporizer 224 to line 241. Optionally, an alkaline gas such as ammonia may flow from alkaline gas container 228, which may be a pressurized tank, through line 229 and pressure regulator 232 to line 241 where it may be combined with the vaporous decontaminant air mixture. Optionally, part of the gaseous air stream may bypass the vaporizer 224 and in doing so flow from the heater 222 through valve 236 and line 237 to line 241. The part of the gaseous air stream that bypasses the vaporizer 224 may be combined with part of the gaseous air stream that flows through the vaporizer 224 in line 241 prior to flowing out of the decontaminant generator 200 through gas outlet 212. The vaporous decontaminant air mixture, whether or not including the alkaline gas, may be referred to as the decontaminant air stream. The decontaminant air stream may flow from outlet 212 through hose 240 to gas inlet 126, and from gas inlet 126 into the shipping container/decontamination chamber 110 wherein the decontamination process may be conducted.

The operation of all electrically powered equipment, including the pump 214, dehumidifier 220, heater 222, vaporizer 224, pump 230, and pressure regulator 232 may be controlled by control unit 238. The control unit may also be used to control ancillary monitors, controllers, and the like, not shown in the drawings.

The decontamination unit 100 may be regarded as being self-contained due to the fact that all of the power required to operate the decontamination unit 100 may be provided by the power generator 300. Alternatively, the power required to operate the decontamination unit 100 may be provided by an outside or local source and as such the use of the power generator 300 may not be required. The power generator 300 may comprise an internal combustion engine combined with an electric generator in a single piece of equipment. Optionally, the power generator 300 may be sufficiently small and lightweight to be stored and transported in the shipping container 110. The power generator 300 may be ruggedized to permit use in hostile environments that may be anticipated for military applications. The power generator 300 may be connected to the decontaminant generator 200 by power cord 302. The power generator 300, when stored and transported in the shipping container 110, may occupy a space in the shipping container 110 equal to about 10% to about 50% of the internal volume of the shipping container 110, and in one embodiment from about 10% to about 30% of the internal volume of the shipping container 110.

The internal combustion engine used in the power generator 300 may comprise any internal combustion engine that is suitable for providing sufficient power to operate the electric generator. The internal combustion engine may be operated using diesel fuel, gasoline, petroleum gas, propane gas, natural gas, liquefied petroleum gas, hydrogen gas, biofuels (e.g., ethanol, biodiesel fuel, etc.), and the like. The internal combustion engine may comprise a spark ignition engine or a compression ignition engine. The internal combustion engine may comprise a two-cycle engine, four-cycle engine, rotary engine, or gas turbine engine. The electric generator used in the power generator 300 may comprise any electric generator that can be powered by the internal combustion engine and provide sufficient power to operate the electrically powered equipment in the decontaminant generator 200. The electric generator may have a power rating in the range from about 2 to about 5 kVA.

An example of a decontaminant generator and a power generator that may be used as the decontamination generator 200 and power generator 300 may be available from STERIS under the trade designation VHP ARD Mobile Biodecontamination System.

Figure 7:
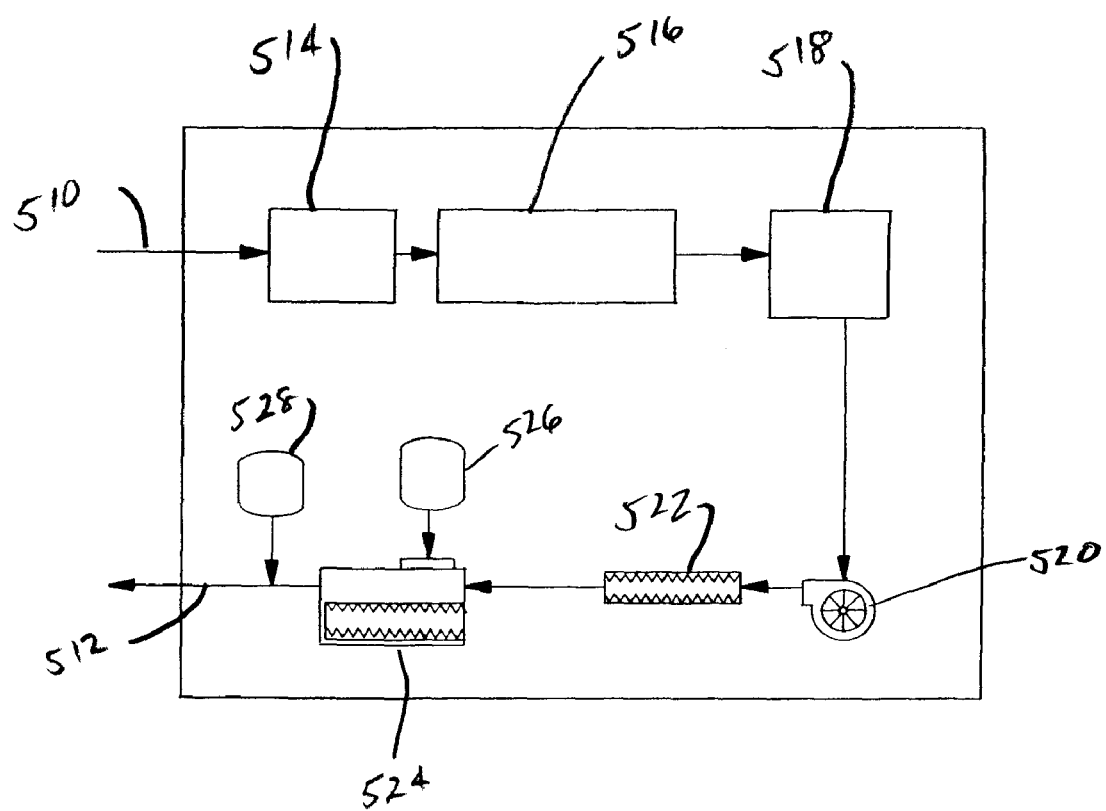
FIG. 7 is a flow sheet showing the operation of the decontaminant generator illustrated in FIG. 6.

An alternate embodiment of the inventive decontamination unit will now be described with reference to FIGS. 5-7. Referring to FIGS. 5-7, decontamination unit 400 comprises shipping container 410. Shipping container 410 is suitable for storing and transporting decontaminant generator 500. The shipping container 410 may be converted to a decontamination chamber during operation of the inventive decontamination process. Shipping container 410 includes sides 414, 415, 416 and 417, bottom 418, and top 419. Shipping container 410 includes latch mechanisms 420 for opening and closing the shipping container 410. Shipping container 410 includes handles 422 to facilitate lifting the shipping container 410.

The shipping container 410 may be of sufficient size to provide for the storage and transport of the decontaminant generator 500, and to provide a decontamination chamber of sufficient scale to accommodate the needs for the desired decontamination process. The shipping container 410 may also be of sufficient size to provide for the storage and transport of hoses, power cables, and other ancillary equipment. The shipping container 410 may be sufficiently lightweight to be readily transportable. The shipping container 410 may be sufficiently air tight to permit operation of the decontamination process in the shipping container at a slightly negative internal pressure, that is, a pressure within the shipping container up to about 10 inches of water below atmospheric pressure, and in one embodiment in the range from about 0.01 to about 5 inches of water below atmospheric pressure, and in one embodiment in the range from about 0.01 to about 2 inches, and in one embodiment in the range from about 0.01 to about 1 inch, and in one embodiment in the range from about 0.01 to about 0.3 inch of water below atmospheric pressure. The shipping container 410 may have an internal volume in the range from about 0.2 to about 1 cubic meter, and in one embodiment in the range from about 0.2 to about 0.5 cubic meter, and in one embodiment in the range from about 0.2 to about 0.4 cubic meter. The shipping container 410 may have a height (as measured from the bottom 418 to the top 419) in the range from about 0.3 to about 1 meter, and in one embodiment in the range from about 0.4 to about 0.8 meter, and in one embodiment in the range from about 0.5 to about 0.7 meters. The shipping container 110 may have a width (as measured from side 414 to side 416) in the range from about 0.4 to about 1 meter, and in one embodiment in the range from about 0.5 to about 0.9 meter, and in one embodiment in the range from about 0.6 to about 0.8 meter. The shipping container 110 may have a length (as measured from side 415 to side 417) in the range from about 0.7 to about 2 meters, and in one embodiment in the range from about 1 to about 1.5 meters, and in one embodiment in the range from about 1.2 to about 1.4 meters. The overall weight of the shipping container 410, when loaded with decontaminant generator 500, may be in the range from about 50 to about 600 pounds (22.7 to 272.2 Kg), and in one embodiment in the range from about 50 to about 300 pounds (22.7 to 136.1 Kg). The shipping container 410 may be readily transported using conventional techniques, for example, the shipping container 410 may be transported by airplane, ship, truck, and the like. The shipping container 410 may be transported using a military standard 463L master pallet.

The shipping container 410 may comprise a shipping case available from Hardigg under the tradename MobilMaster 24. The MobilMaster 24, which is illustrated in FIG. 5, has outer dimensions of 1.31×0.696×0.594 meters, an internal volume of 0.385 cubic meters, and a shipping weight of 26.0 Kg. The MobilMaster 24 is made of rotational molded polyethylene, and is designed to stack 24 cases cubed out (4 layers, 6 cases in each layer) on a 463L pallet.

In the practice of the inventive decontamination process, the shipping container 410 may be opened and the decontaminant generator 500 may be removed. The shipping container 410 may be turned on its side. The shipping container 410 is equipped with gas inlet 426 and gas outlet 428. The gas inlet 426 and gas outlet 428 may be connected to hoses 440 and 442. The hoses 440 and 442 may be connected and extend from the gas inlet 426 and gas outlet 428 to the decontaminant generator 500 to provide for the flow of a decontaminant air stream from the decontaminant generator 500 to the gas inlet 426, and the flow of gas from the gas outlet 428 back to the decontaminant generator 500. The shipping container 410 may be equipped with bulkhead connections to facilitate the use of concentration monitors, etc. The contaminated articles to be decontaminated may be loaded in the shipping container 410. The shipping container 410 may then be closed. A decontaminant air stream may then flow from the decontaminant generator 500 through hose 440 to gas inlet 426, and from gas inlet 426 into the interior of the shipping container 410. When used in the operation of a decontamination process, the shipping container 410 may be referred to as a decontamination chamber. The decontaminant air stream may circulate in the interior of the shipping container/decontamination chamber 410, contact contaminated articles positioned in the shipping container/decontamination chamber 410, and decontaminate the contaminated articles. A gaseous air stream comprising spent gases (i.e., air, residual decontaminant, residual hazardous biological and/or chemical materials, etc.) may flow through gas outlet 428, and from gas outlet 428 through hose 442 back to the decontaminant generator 500. The decontamination process may be controlled using control unit 506.

The shipping container 410 may include interior shelves 440. The shelves 440 may be used to facilitate placement of contaminated articles in the shipping container/decontamination chamber 410 during operation of the decontamination process. Any desired number of shelves 440 may be used. The shelves 440 may be removable. The shelves 440 may be perforated or grated. The use of perforated or grated shelves may be advantageous to permit enhanced gas circulation within the shipping container/decontamination chamber 410.

The decontaminant generator 500 may comprise housing 502 and control unit 506. The housing 502 may include doors 504. The decontaminant generator 500 may include gas inlet 510, gas outlet 512, catalytic converter 514, filter 516, desiccant cartridge 518, blower 520, heater 522, vaporizer 524, liquid decontaminant container 526, and alkaline gas container 528. The power to operate the decontaminant generator 500 may be provided by an outside or local source.

The decontaminant generator 500 may occupy a space in the shipping container 410 equal to about 30% to about 99% of the internal volume of the shipping container 410, and in one embodiment from about 50% to about 95% of the internal volume, and in one embodiment from about 70% to about 95% of the internal volume of the shipping container 410. The decontaminant generator 200 may have a weight in the range from about 50 to about 500 pounds (22.7 to 226.8 Kg).

In the operation of the decontaminant generator 500, a gaseous air stream comprising spent gases from the decontamination process may flow from the shipping container/decontamination chamber 410 through hose 442 back to the decontaminant generator 500. The gaseous air stream may enter the decontaminant generator 500 through gas inlet 510. The gaseous air stream may flow through catalytic converter 514 to and through filter 516, and from the filter 516 to and through desiccant cartridge 518. The catalytic converter 514 may be used to destroy residual amounts of the decontaminant that may be in the gaseous air stream. For example, the catalytic converter 514 may be use to convert residual hydrogen peroxide to water vapor and oxygen. The catalyst may comprise any transition metal, transition metal oxide, or combination thereof, having the desired catalytic properties. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The filter 516 may comprise a carbon filter and a HEPA filter. The desiccant cartridge 518 may contain a desiccant material such as lithium chloride, silica gel, molecular sieves, and the like. The desiccant material may be used to absorb moisture from the gaseous air stream and thereby dehumidify the gaseous air stream. The gaseous air stream may flow from the desiccant cartridge 518 through blower 520 to heater 522 where it may be heated. The gaseous air stream may flow from the heater 522 into vaporizer 524. Liquid decontaminant may flow from liquid decontaminant container 526 into the vaporizer 524. The liquid decontaminant may be vaporized in vaporizer 524 and combined with the gaseous air stream. The vaporous decontaminant air mixture may flow out of the vaporizer 524 through line 512. Optionally, an alkaline gas such as ammonia may flow from alkaline gas container 528, which may be a pressurized cartridge, to line 512 where it may be combined with the vaporous decontaminant air mixture.

The decontaminant may comprise one or more oxidants such as peracids (e.g., peracetic acid) and/or peroxides (e.g., hydrogen peroxide), and the like. Oxidants such as hypochlorites, ozone, and the like, may be used. Mixtures of two or more of these may be used. Aqueous solutions of these oxidants may be used. The decontaminant may be combined with a solvent. The solvent may be miscible with water. When the decontaminant comprises hydrogen peroxide, the solvent may be used to enhance the solubility of the hydrogen peroxide and its associated decomposition products in the contaminant and thereby enhance the rate of destruction of the contaminant. The solvent may comprise a mixture of water and tert-butyl alcohol; water and acetonitrile; or water, acetonitrile and isopropyl alcohol. Other suitable solvents may include tetrahydrofuran, dimethylsulfoxide, acetone, acetaldehyde, propylene oxide, acetamide, diethylamine, dimethoxyethane, or a mixture of two or more thereof. The solvent concentration in the combined mixture of decontaminant and solvent may be in the range up to about 60% by weight solvent, and in one embodiment in the range from about 20 to about 60% by weight solvent. The decontaminant may be combined with an alkaline gas such as ammonia in applications wherein an increase in the pH of the decontaminant may be desired.

Vaporous hydrogen peroxide (VHP), which may be generated from an aqueous solution of hydrogen peroxide, may be used as the decontaminant. The aqueous solution may comprise from about 30% to about 40% by weight hydrogen peroxide, and in one embodiment about 35% by weight hydrogen peroxide; and from about 60% to about 70% by weight water, and in one embodiment about 65% by weight water. By adding an alkaline gas that is soluble in the hydrogen peroxide (ammonia, for example), the pH of the decontaminant may be controlled. The presence of hydrogen peroxide in the decontaminant may serve to lower the pH (35% aqueous hydrogen peroxide solution has a pH of about 3 to about 4) and the ammonia may be added to raise the pH to a value of about 8 to about 9. The volumetric ratio of VHP to ammonia gas may be in the range from about 1:1 to about 1:0.0001.

VHP, when used in combination with ammonia gas, may be referred to as modified VHP or mVHP. VHP and/or mVHP may be effective microbial and chemical decontaminants because they may provide a broad spectrum of activity against a wide variety of pathogenic microorganisms and chemical pathogenic agents, such as hard to destroy spores of *Bacillus stearothermophilus*, *Bacillus anthracis*, smallpox virus, and the like. They may be also effective at or close to room temperature (e.g., about 15 to about 30° C.), making them suitable for use in the shipping container/decontamination chamber 110 or 410 with little or no heating. VHP and/or mVHP may have good material compatibility, rendering them safe for use with a variety of equipment and materials, including electronic equipment, and the like. VHP may degrade to water and oxygen over time, which may not be harmful to a person subsequently opening the shipping container/decontamination chamber 110 or 410. Low levels of hydrogen peroxide (for example, about 1 ppm, or less) that may remain in the shipping container/decontamination chamber 110 or 410 after the decontamination process has been completed may not be considered to pose a risk to a person opening the shipping container/decontamination chamber.

The progress of the decontamination process may be monitored using one or more decontamination or sterilization indicators. These indicators may contain a biological indicator. The biological indicator may comprise one or more test organisms which may be more resistant to the decontamination process than the organisms to be destroyed by the decontamination process. The test organism may be placed in contact with an incubation medium to determine whether the decontamination process was effective.

The temperature of the decontaminant air stream entering the shipping container/decontamination chamber 110 or 410, as well as the temperature within the shipping container/decontamination chamber, may be in the range from about 10° C. to about 50° C., and in one embodiment in the range from about 15° C. to about 50° C., and in one embodiment in the range from about 15° C. to about 30° C. The relative humidity of the decontaminant air stream entering the shipping container/decontamination chamber 110 or 410 may be in the range from about 0 to about 50%, and in one embodiment in the range from about 20 to about 40% by volume. The term "relative humidity" is used herein to refer to the ratio of the partial pressure of water vapor in the decontaminant air stream to the saturated vapor pressure of water at the temperature of the decontaminant air stream expressed in terms of percentage. The concentration of decontaminant in the decontaminant air stream entering the shipping container/decontamination chamber 110 or 410 may be in the range from about 0.01 to about 2% by volume, and in one embodiment in the range from about 0.01 to about 1.5% by volume, and in one embodiment in the range from about 0.01 to about 1% by volume, and in one embodiment in the range from about 0.01 to about 0.5% by volume, and in one embodiment in the range from about 0.02 to about 0.2% by volume, and in one embodiment in the range from about 0.02 to about 0.05% by volume. When the decontaminant comprises solvent, the concentration of decontaminant plus solvent in the decontaminant air stream entering the shipping container/decontamination chamber 110 or 410 may be in the range from about 0.01 to about 0.3% by volume, and in one embodiment in the range from about 0.02 to about 0.08% by volume. When the decontaminant comprises an alkaline gas, the concentration of alkaline gas in the decontaminant air stream entering the shipping container/decontamination chamber 110 or 410 may be in the range from about 0.001 to about 0.01% by volume, and in one embodiment in the range from about 0.003 to about 0.005% by volume. The gas flow rate through the shipping container/decontamination chamber 110 or 410 may be in the range from about 5 to about 40 cubic feet per minute (CFM) (0.14 to 1.13 cubic meters per minute (CMM)), and in one embodiment in the range from about 8 to about 20 CFM (0.23 to 0.57 CMM). The operating pressure within the shipping container/decontamination chamber 110 or 410 may be slightly negative to prevent the leakage of contaminants and decontaminants from the shipping container/decontamination chamber 110 or 410. The internal pressure may be in the range of up to about 10 inches of water below atmospheric pressure, and in one embodiment in the range from about 0.01 to about 5 inches of water, and in one embodiment in the range from about 0.01 to about 2 inches of water, and in one embodiment in the range from about 0.01 to about 1 inch of water, and in one embodiment in the range from about 0.01 to about 0.5 inch of water, and in one embodiment in the range from about 0.01 to about 0.3 inch of water.

When the decontaminant air stream flows into the shipping container/decontamination chamber 110 or 410 and contacts the contaminated articles to be decontaminated, the process may be regarded as a dry process characterized by the absence of condensate formation on the surfaces of the contaminated articles being decontaminated. Alternatively, the process may be regarded as a wet process characterized by the formation of a condensate in the form of a liquid film on the surfaces of the contaminated articles. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide.

The contaminated articles may be contaminated with any contaminant. The articles may comprise any article that may be stored in the shipping container/decontamination chamber 110 or 410. These may include military weapons, clothing, body armor, as well as sensitive equipment such as computers, test equipment, optical devices, electronic devices, communications equipment, and the like. These may include radio headsets and night vision goggles, as well as other small high value pieces of equipment. The contaminant may comprise one or more chemical, biological, radiological and/or nuclear (CBRN) warfare agents.

Different levels of decontamination may be accomplished within the shipping container/decontamination chamber 110 or 410. As used herein, the term "decontamination," may encompass both microbial decontamination as well as chemical decontamination—the destruction of chemical agents, or their conversion to harmless or odorless compounds. Decontamination may also encompass the neutralizing of unpleasant odors, such as tobacco smoke, perfume, or body odor residues, and odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination may encompass sterilization, the highest level of biological contamination control, which connotes the destruction of all living microorganisms. The term may also include disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed in the decontamination process include bacterial spores, vegetative bacteria, viruses, molds, and fungi. Some of these may be capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

The decontamination units 100 and 400 may be used in hostile environments such as those that may be anticipated for military applications. When intended for use in such hostile environments, the shipping containers 110 and 410, and in one embodiment also the decontaminant generators 200 and 500, and/or the power generator 300, may be ruggedized. The shipping containers 110 and 410 may be insulated. The shipping containers 110 and 410 may be constructed in compliance with military standard MIL-STD-810. The shipping container 110 and 410, and optionally the decontaminant generators 200 and 500, may be constructed of materials capable of withstanding exposure to decontaminants that may be used in the decontamination process and contaminants which may be encountered. The shipping containers 110 and 410, and optionally the decontaminant generators 200 and 500, and/or the power generator 300, may be constructed using any material that is sufficient to provide the apparatus with the required properties of strength and lightweight as well as the desired level of ruggedization. Ruggedization may include providing resistance to anticipated operating conditions and hazards that may be hostile, including hot and cold temperatures, exposure to solar radiation, rain, fungus, salt fog, sand, dust, vibration and/or shock, as well as exposure to CBRN contaminants. The materials of construction may include stainless steel, coated steel, aluminum, anodized aluminum, and the like. Various metal alloys may be used, including the stainless steel alloys SS304 and SS316, and aluminum alloy 6061. Non-reactive materials, such as polytheylene, polyvinyl chloride, fluorinated polymers such as polytetrafluoroethylene, and the like, may be used.

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A self-contained transportable decontamination unit, comprising:
   a shipping container and a decontaminant generator, the shipping container configured to transport the decontaminant generator, the shipping container configured as a decontamination chamber, the shipping container including at least one gas inlet for admitting a decontaminant air stream into the shipping container and at least one gas outlet for removing gas from the shipping container, the shipping container constructed of a rigid material and being stackable with one or more other shipping containers during transport of the decontamination generator;
   a military master pallet on which the shipping container is positioned; and
   a power generator for generating power to operate the decontaminant generator, the power generator being adapted for being stored in the shipping container during transport of the shipping container and being removed from the shipping container when used to conduct the decontamination;
   the decontaminant generator being adapted for generating a decontaminant air stream, the decontaminant generator being adapted for being stored in the shipping container during transport of the shipping container and being removed from the shipping container when used to conduct a decontamination, the decontaminant generator having a decontaminant air stream outlet which is adapted to be connected to the gas inlet of the shipping container, the decontaminant generator having a gas inlet which is adapted to be connected to the gas outlet of the shipping container,
   wherein the shipping container is ruggedized.

2. The decontamination unit of claim 1 wherein the shipping container has an internal volume in the range from about 0.5 to about 2 cubic meters.

3. The decontamination unit of claim 1 wherein the shipping container has an internal volume height in the range from about 0.2 to about 1 cubic meter.

4. The decontamination unit of claim 1 wherein the shipping container when loaded with the decontaminant generator has a weight in the range from about 200 to about 700 pounds.

5. The decontamination unit of claim 1 wherein the shipping container when loaded with the decontaminant generator has a weight in the range from about 50 to about 600 pounds.

6. The decontamination unit of claim 1 wherein the decontaminant generator comprises a housing, gas inlet, gas outlet, catalytic converter, filter, desiccant cartridge, blower, heater, vaporizer, liquid decontaminant container, and alkaline gas container.

7. The decontamination unit of claim 1 wherein the power generator comprises an internal combustion engine and an electric generator.

8. The decontamination unit of claim 7 wherein the internal combustion engine and the electric generator are combined in a single piece of equipment.

9. The decontamination unit of claim 1 wherein the decontaminant generator and/or power generator are ruggedized.

\* \* \* \* \*